US010185809B1

(12) United States Patent
Zhou et al.

(10) Patent No.: US 10,185,809 B1
(45) Date of Patent: Jan. 22, 2019

(54) PATIENT PROJECTION METHODOLOGY

(71) Applicant: IMS Health Incorporated, Danbury, CT (US)

(72) Inventors: Li Zhou, Yardley, PA (US); Xiaoping Cai, Newtown, PA (US); Timothy A. Hughes, Ambler, PA (US)

(73) Assignee: IQVIA Inc., Parsippany, NJ (US)

( * ) Notice: Subject to any disclaimer, the term of this patent is extended or adjusted under 35 U.S.C. 154(b) by 209 days.

(21) Appl. No.: 14/054,272

(22) Filed: Oct. 15, 2013

(51) Int. Cl.
*G06Q 30/02* (2012.01)
*G06Q 50/22* (2018.01)
*G06F 19/00* (2018.01)

(52) U.S. Cl.
CPC ..... *G06F 19/3456* (2013.01); *G06Q 30/0202* (2013.01); *G06Q 30/0205* (2013.01); *G06Q 50/22* (2013.01)

(58) Field of Classification Search
CPC .... G06Q 50/22; G06Q 50/24; G06Q 30/0202; G06Q 30/0205; G06F 21/6254; G06F 19/3456
USPC ........................................................ 705/2–3
See application file for complete search history.

(56) References Cited

U.S. PATENT DOCUMENTS

| 8,239,218 | B1 * | 8/2012 | Madras | G06F 19/322 |
| | | | | 705/2 |
| 2004/0260599 | A1 * | 12/2004 | Ziegele | G06Q 30/02 |
| | | | | 705/7.31 |
| 2005/0268094 | A1 * | 12/2005 | Kohan | G06F 21/6254 |
| | | | | 713/165 |
| 2006/0116908 | A1 * | 6/2006 | Dew | G06F 19/00 |
| | | | | 705/2 |
| 2008/0168042 | A1 * | 7/2008 | Dettinger | G06F 17/30424 |
| 2008/0171916 | A1 * | 7/2008 | Feder | G06F 19/00 |
| | | | | 600/300 |
| 2011/0039269 | A1 * | 2/2011 | Cowens | C12Q 1/6886 |
| | | | | 435/6.11 |

* cited by examiner

*Primary Examiner* — Joy Chng
(74) *Attorney, Agent, or Firm* — Fish & Richardson P.C.

(57) ABSTRACT

The disclosure generally describes computer-implemented methods, software, and systems for projecting patients having a medical condition by utilizing multiple data sources. One computer-implemented method includes accessing patient data related to multiple patient transactions, each patient transaction representing provision of medical care including one or more pharmaceutical products to a patient. One or more factors are derived for use in projecting the accessed patient data to represent all patient transactions for the geographic area. A first projection of the accessed patient data is calculated using the derived one or more factors. The first calculated projection is compared to pharmaceutical distribution data for the geographic area. The derived factors are adjusted by reducing a difference between one or more components of the first calculated projection and one or more components of the pharmaceutical distribution data. A second projection of the accessed patient data is calculated using the adjusted one or more factors.

20 Claims, 3 Drawing Sheets

PATIENT PROJECTION METHODOLOGY

BACKGROUND

It may be hard to track patients with complex medical conditions, particularly when they receive their treatment from many different entities (e.g., hospitals, clinics, and pharmacies). Tracking these patients is made even more difficult by privacy laws that regulate the exchange of patient data between healthcare providers. As a result, any given entity often only has access to its own data. For example, a pharmaceutical company may only have access to data regarding the distribution of its products without a view into the patients that ultimately utilize those products, much less details regarding the patients' overall treatment or diagnosis.

SUMMARY

The present disclosure relates to computer-implemented methods, software, and systems for rating and ranking stakeholders in the distribution of controlled substances. One computer-implemented method includes accessing patient data related to multiple patient transactions, each patient transaction representing provision of medical care including one or more pharmaceutical products to a patient, and the accessed patient data representing a sample of all patient transactions for a geographic area; deriving one or more factors for use in projecting the accessed patient data to represent all patient transactions for the geographic area; calculating a first projection of the accessed patient data using the derived one or more factors; comparing the first calculated projection to pharmaceutical distribution data for the geographic area, the pharmaceutical distribution data representing a census of sales of the one or more pharmaceutical products to medical facilities at which the administration of medical care took place within the geographic area; based on the comparison of the first calculated projection to the pharmaceutical distribution data, adjusting the derived factors by reducing a difference between one or more components of the first calculated projection and one or more components of the pharmaceutical distribution data; and calculating a second projection of the accessed patient data using the adjusted one or more factors.

Other implementations of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of software, firmware, or hardware installed on the system that in operation causes or causes the system to perform the actions. One or more computer programs can be configured to perform particular operations or actions by virtue of including instructions that, when executed by a data processing apparatus, cause the apparatus to perform the actions.

These and other embodiments may each optionally include one or more of the following features. For instance, the accessed patient data may be received from a plurality of source types, the plurality of source types including pharmacy outlets, out-patient clinics, and hospitals; deriving the one or more factors may include deriving separate factors for each of the plurality of source types from which patient data has been received; calculating the first projection may include separately calculating separate first projections for each of the plurality of source types based on the separate factors derived for each source type; comparing the first calculated projection to pharmaceutical distribution data for the geographic area may include comparing the separate first projections for each of the plurality of source types with pharmaceutical distribution data associated with each of the plurality of source types; and adjusting the derived factors may include separately adjusting the factors derived for each source type based on the comparison of the separate first projections for each of the plurality of source types with pharmaceutical distribution data associated with each of the plurality of source types.

The method may further include aggregating the accessed patient data based on anonymous tracking identifiers included in each of the multiple patient transactions. The method may further include comparing one or more components of the second projection to one or more components of claims data received from health insurance companies; and validating the second projection based on the comparison of the one or more components of the second projection to the one or more components of the claims data.

The geographic area may be a national area that includes sub-national segments. Comparing the first calculated projection to pharmaceutical distribution data for the geographic area may include comparing the first calculated projection for the national area to pharmaceutical distribution data for the national area and comparing the first calculated projection for each sub-national segment to pharmaceutical distribution data for each sub-national segment; and adjusting the derived factors may include adjusting the derived factors by reducing a difference between one or more components of the first calculated projection for the national area and one or more components of the pharmaceutical distribution data for the national area, and adjusting the derived factors by reducing a difference between one or more components of the first calculated projection for each sub-national segment and one or more components of the pharmaceutical distribution data for each sub-national segment.

The method may further include associating additional patient characteristics with the accessed patient data. Calculating the second projection may include calculating a projection of the additional patient characteristics to the entire geographic area. The additional patient characteristics may include metastic and stage information for oncology patients.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

This disclosure generally describes computer-implemented methods, software, and systems for projecting patients having a medical condition by utilizing multiple sources of data.

For illustration purposes, the various implementations described herein will be described with regard to a patient projection system that receives and analyzes medical data from multiple sources. As will be described in greater detail below, the patient projection system provides an accurate market view of patients with a medical condition at a much more granular level than previously possible. Moreover, the patient projection system provides an increased capability to conduct custom patient analysis and generate custom reports. For ease of explanation, various implementations described herein will be described with regard to the projection of oncology patients. However, the patient projection system is not limited to any particular medical condition, and is equally applicable to any medical condition.

Figure 1:
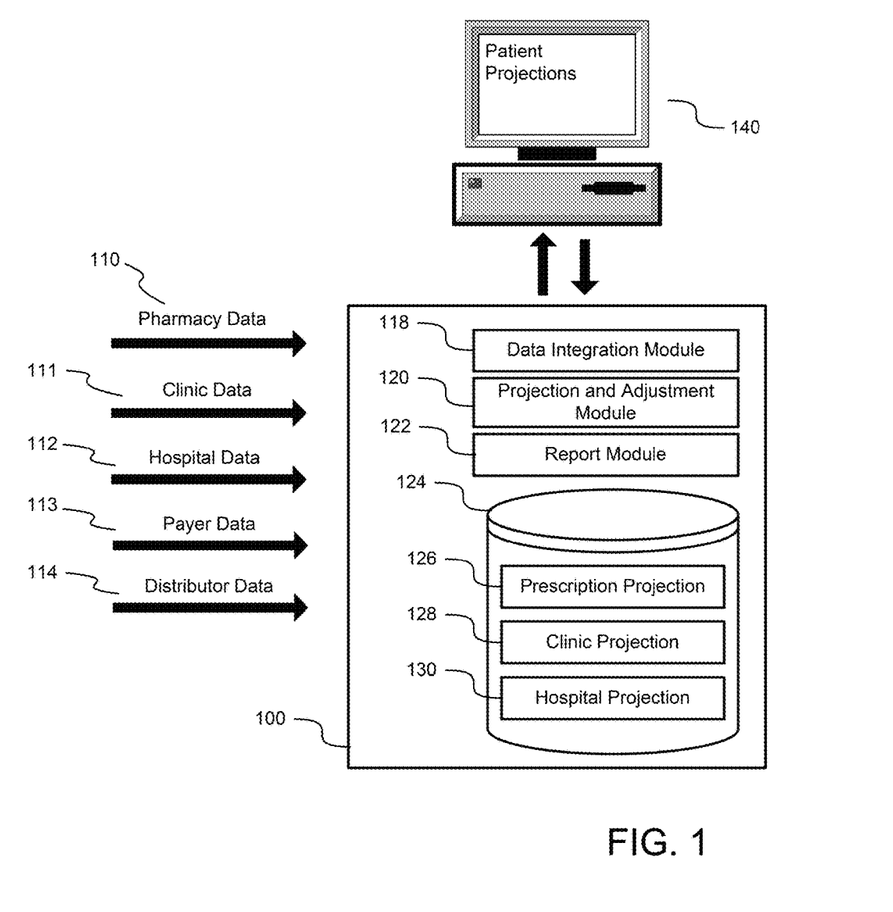
FIG. 1 is a block diagram illustrating an example system for projecting patients having a medical condition by utilizing multiple sources of data.

FIG. 1 illustrates an example patient projection system implemented in a computing system 100 configured for projecting patients having a medical condition by utilizing multiple sources of data. At a high-level, the illustrated example computing system 100 receives various data from pharmacies 110, clinics 111, hospitals 112, payers 113, and distributors 114.

The pharmacy data 110 may include data regarding prescriptions dispensed in the retail and non retail sector. The pharmacy data 110 may be received, for example, from one or more pharmacy outlets and represent data reflecting all pharmacy products dispensed by the one or more outlets, including information about the type of prescription used to obtain the product and the payment method used to purchase the product. The one or more pharmacy outlets, which may include pharmacy chains, independent pharmacies, long-term care facilities, and/or mail services, may provide the pharmacy data 110 on a periodic basis (e.g., every day, week, or month). Additionally or alternatively, the pharmacy data 110 may be collected by one or more other data collection systems and then provided to the computing system 100.

The clinic data 111 may include anonymized physician diagnoses from either clinic office insurance claim form or electronic medical records. The clinic data 111 may, for example, include diagnoses, treatments, and injectable medications, in-office procedures, lab orders, and/or patient demographics. The clinic data 111 from electronic medical records provides data with more complete patient treatment information, like lab test and test results, and vitals. In some implementations, the clinic data 111 may include an identifier for linking an anonymous patient's diagnosis data to other data related to the patient (e.g., pharmacy data 110). Additionally or alternatively, the clinic data 111 may be collected by one or more other data collection systems and then provided to the computing system 100.

The hospital data 112 may include anonymized patient treatment information included in-patient and out-patient records. The hospital data 112 may, for example, be received from general medical-surgical and specialty hospitals that agree to provide data. Specifically, the hospital data 112 may include detailed diagnoses, administered procedures, administered drugs, utilized devices, applied charges, sites of service, patient demographics, and/or admission/discharge characteristics. In some implementations, the hospital data 112 may include an identifier for linking an anonymous patient's treatment data to other data related to the patient (e.g., pharmacy data 110 and/or clinic data 111). Additionally or alternatively, the hospital data 112 may be collected by one or more other data collection systems and then provided to the computing system 100.

The payer data 113 may include information about anonymized patient medical and pharmaceutical claims. The payer data 113 may be received for example from one or more health insurance companies. Specifically, the payer data 113 may include, for each claim, diagnoses, administered procedures, retail and mail order prescriptions, in-patient details (e.g., admitting diagnosis, and admission source and type), provider/pharmacy ID, costs of services and/or prescriptions, place of service, and/or plan type and time enrolled. In some implementations, the payer data 113 may include an identifier for linking an anonymous patient's treatment data to other data related to the patient (e.g., pharmacy data 110, clinic data 111, and/or hospital data 112). Additionally or alternatively, the payer data 113 may be collected by one or more other data collection systems and then provided to the computing system 100.

The distribution data 114 may include information about pharmaceutical purchases made from distributors (e.g., pharmaceutical wholesalers or manufacturers) by one or more pharmacy outlets, clinics, and/or hospitals. For example, the distribution data 114 may include information about the distributor from which an amount of a pharmaceutical product is purchased, the type of pharmaceutical product purchased, the location of both the purchaser and seller of the pharmaceutical product, when the purchase was conducted, and/or the amount of a pharmaceutical product that was purchased. In some implementations, the pharmaceutical distributors may provide the distribution data 114 regarding the pharmaceutical products the distributors have sold. Additionally or alternatively, the distribution data 114 may be collected by one or more other systems and then provided to the computing system 100.

The pharmacy data 110, clinic data 111, hospital data 112, payer data 113, and distribution data 114 may be collected in any suitable fashion and may represent either sample or census data. In some implementations, for example, the pharmacy data 110, clinic data 111, hospital data 112, and payer data 113 are generally sample data, and thus only represent a portion of the total population of entities. Accordingly, the pharmacy data 110, clinic data 111, hospital data 112, and payer data 113 may need to be projected to larger population (e.g., to a nation level) in order to provide a complete view of that larger population. On the other hand, in some implementations, the distribution data 114 may be census data that represents all or nearly all of the pharmaceutical sales made by distributors at a national level. Accordingly, the distribution data 114 may be considered true data and used as the benchmark for the projection.

The pharmacy data 110, clinic data 111, hospital data 112, payer data 113, and distribution data 114 may be acquired/received by a third-party operator of the computing system 100 from many different companies and/or entities within all levels the medical/healthcare industry. Thus, the received pharmacy data 110, clinic data 111, hospital data 112, payer data 113, and distribution data 114 may represent a much wider breadth of information than the information to which any one company and/or actor within the medical/healthcare industry would individually have access. Moreover, whether collected by the computing system 100 or acquired from one or more third parties, the received pharmacy data 110, clinic data 111, hospital data 112, payer data 113, and distribution data 114 is de-identified in such a manner as to comply with all relevant patient privacy and protection laws of whichever country the data is acquired from and/or used in (e.g., the Health Insurance Portability and Accountability Act of 1996).

For illustrative purposes, computing system 100 will be described as including a data integration module 118, a projection and adjustment module 120, a report module 122, and a storage device 124. However, the computing system 100 may be any computing platform capable of performing the described functions. For example, the computing system 100 may include one or more servers that may include hardware, software, or a combination of both for performing the described functions. Moreover, the data integration module 118, projection and adjustment module 120, and report module 122 may be embodied together or separately in hardware and/or software. Though the data integration module 118, projection and adjustment module 120, and report module 122 will be described as each carrying out certain functionality, the described functionality may be performed by one or more other modules in conjunction with or in place of the described module.

The data integration module 118 receives and integrates the pharmacy data 110, clinic data 111, hospital data 112, payer data 113, and distribution data 114 into a relational storage model (e.g., database or data warehouse). Before integrating the received data, the data integration module 118 may pre-process the pharmacy data 110, clinic data 111, hospital data 112, payer data 113, and distribution data 114 for specific information. For example, the data integration module 118 may de-duplicate the received retail prescription data 110, encrypted patient data 112, reference prescriber data 114, and pharmaceutical purchase data 116.

As described above, the pharmacy data 110, clinic data 111, hospital data 112, payer data 113, and distribution data 114 may each include a linking identifier. The linking identifier provides a mechanism for identifying an anonymous patient across multiple sources of data. The linking identifier may be produced at the source of data and included with the data as it is originally collected by the data integration module 118 or the data integration module 118 may produce the linking identifier by analyzing the received data. In either case, the data integration module 118 determines that records from different sources (e.g., pharmacy data 110, clinic data 111, hospital data 112, payer data 113, and/or distribution data 114) are associated with the same tacking identifier and thus represent a single patient.

In some implementations, after the data integration module 118 pre-processes and/or links the received data, the data integration module 118 organizes and stores the received pharmacy data 110, clinic data 111, hospital data 112, payer data 113, and distribution data 114 into one or more relational data structures in one or more storage devices 124. For example, the data integration module 118 may organize and store the received pharmacy data 110, clinic data 111, hospital data 112, payer data 113, and distribution data 114 into a relational database that permits the received data to be searched and visualized according to any number of shared keys within the received data (e.g., service provider name, service provider location, diagnosis, pharmaceutical product prescribed/filled, and/or tracking identifier of the patient). This centralized repository of the received information may provide a more efficient basis for the projections described herein, as well as any other customized studies involving this data.

As will be describe in greater detail below with regard to FIG. 2, the projection and adjustment module 120 utilizes the pharmacy data 110, clinic data 111, hospital data 112, payer data 113, and distribution data 114 integrated by the data integration module 118 to project patients with a medical condition for a given geographic area. In some implementations, for example, the pharmacy data 110, clinic data 111, and hospital data 112 represent a sample of data from across a country. In particular, the pharmacy data 110 may represent prescription data received from a subset of all the pharmacies in the country. Similarly, the clinic data 111 may represent patient diagnosis data received from a subset of all the out-patient medical offices in the country. The hospital data 112 may represent patient treatment data received from a subset of all the in-/out-patient hospitals in the country.

The projection and adjustment module 120 may derive one or more factors for projecting each of the pharmacy data 110, clinic data 111, and hospital data 112 such that the resulting prescription projection 126 estimates the pharmacy data for all of the pharmacies in the country, the clinic projection 128 estimates the clinic data for all of the out-patient medical offices in the country, and the hospital projection 130 estimates the pharmacy data for all of the in-/out-patient hospitals in the country. However, these initial projections may be biased due to the sources of data.

Accordingly, the projection and adjustment module 120 adjusts the derived one or more factors to further refine the resulting projections. In some implementations, for example, the projection and adjustment module 120 may use distributor data 114 as part of the adjustments. The distributor data 114 may represent all or nearly all sales of pharmaceutical products to the pharmacies, clinics, and hospitals in the country. In other words, the distributor data 114 may represent a census view of the pharmaceutical products going into all of the pharmacies, clinics, and hospitals in the country. Relatedly, the pharmacy data 110, clinic data 111, and hospital data 112 may each include information about the administration or prescription of pharmaceutical products to patients. In other words, the pharmacy data 110, clinic data 111, and hospital data 112 may provide an indication of all or nearly all the pharmaceutical products going out of a sample of pharmacies, clinics, and hospitals.

The projection and adjustment module 120 uses the distributor data 114 to adjust the one or more derived factors such that the projection of the pharmacy data 110, clinic data 111, and hospital data 112 to all of the pharmacies, clinics, and hospitals results in a projection of the amount of pharmaceutical products going out of these pharmacies, clinics, and hospitals that correlates to the known amount of pharmaceutical products going into all of the pharmacies, clinics, and hospitals.

The projection and adjustment module 120 may optionally further adjust and validate the one or more factors. In some implementations, for example, the projection and adjustment module 120 may use payer data 113 to validate each of the projections of the pharmacy data 110, clinic data 111, and hospital data 112. Additionally or alternatively, patient indication data may be used to validate the one or more factors and resulting projections. For example, the projection and adjustment module 120 may aggregate the projected patients by drug and indication across the pharmacy data 110, clinic data 111, and hospital data 112. The projection and adjustment module 120 may then determine or receive information about differences between different sources of data (e.g. pharmacy data 110, clinic data 111, hospital data 112, and payer data 113), and adjustment the one or more factors to provide a reliable indication distribution and trend.

The projection and adjustment module 120 may also optionally integrate additional patient information (e.g., condition-specific information or consumer information) to the existing projections and project this additional information to the total population of patients. In some implementations, for example, the projection and adjustment module 120 may determine metastatic or stage status for a sample of oncology patients. The projection and adjustment module 120 may derive statistical models using the one or more adjusted factors to project this metastatic or stage status to the total population of oncology patients in a geographic area. Similarly, the projection and adjustment module 120 may model any customized studies based on the one or more adjusted factors and the received pharmacy data 110, clinic data 111, hospital data 112, payer data 113, and distribution data 114.

The report module 122 prepares reports based on the projections generated by the projection and adjustment module 120. The reports prepared by the report module 122 may include one or more of the projections calculated by the projection and adjustment module 120 as well as any other data contained in the pharmacy data 110, clinic data 111, hospital data 112, payer data 113, and distribution data 114.

The reports generated by the report module 122 may be filtered based on any one or more criteria included in the pharmacy data 110, clinic data 111, hospital data 112, payer data 113, and distribution data 114. For example, the report module 122 may filter reports based on location, type of pharmaceutical product, medical specialty of a prescriber, and/or medical condition. In other words, any data received and processed by the projection and adjustment module 118 or any projections calculated by the projection and adjustment module 120 may be included in or used to filter the data included a report generated by report module 122.

Additionally, in some implementations, the reports generated by the report module 122 may be either dynamic or static. For example, the report module 122 may generate a report that includes data presented in one or more static formats (e.g., a chart, a graph, or a table) without providing any mechanism for altering the format and/or manipulating the data presented in the report. In some implementations, for example, the report module 122 may provide a static report in a PDF, spreadsheet, or XML format.

Additionally or alternatively, the report module 122 may generate a report that includes controls allowing a user to alter and/or manipulate the report itself. For example, the report module 122 may provide a dynamic report in the form of an HTML document that includes controls for filtering, manipulating, and/or ordering the data displayed in the report. Moreover, a dynamic report may include the capability of switching between numerous visual representations of the included in the dynamic report. In some implementations, a dynamic report may provide direct access to some or all of the pharmacy data 110, clinic data 111, hospital data 112, payer data 113, and/or distribution data 114 in an aggregated or un-aggregated form, prepared by the data integration module 118 and/or the projection and adjustment module 120, as opposed to allowing access to only data and/or projections included in the report itself. An example of a report generated by the report module 122 will be described with regard to FIG. 3.

One or more clients 140 may interface with the computing system 100 to request and receive reports created by the report module 122. In some implementations, for example, the one or more clients 140 may include a web browser that provides Internet-based access to the computing system 100. Through the web browser, a user of a client 140 (e.g., a pharmaceutical company) may request a static or dynamic report from the report module 122.

In some implementations, access to the computing system 100 may be controlled in order to protect any confidential data stored in the computing system 100. For example, in some implementation, each user of a client 140 that attempts to request a report from the computing system 100 may be required to use a log in ID created by the owner/operator of the system 100 (e.g., IMS Health) and create a password to log into a user account. The user accounts may include identifying information about the user that may be used to limit the user's access to particular types of data, reports, and/or other functionality. For example, a user account associated with a particular company may limit the company to only viewing projections related to that particular company's products.

There may be any number of clients 140 associated with, or external to, the example computing system 100. For example, while the illustrated example computing system 100 is shown in communication with one client 140, alternative implementations of the example computing system 100 may communicate with any number of clients 140 suitable to the purposes of the example computing system 100. Further, the term "client" and "user" may be used interchangeably as appropriate without departing from the scope of this disclosure. Moreover, while the client 140 is described in terms of being used by a single user, this disclosure contemplates that many users may use one computer, or that one user may use multiple computers.

The illustrated client 140 is intended to encompass any computing or communication device such as a desktop computer, laptop/notebook computer, wireless data port, smart phone, personal data assistant (PDA), tablet computing device, one or more processors within these devices, or any other suitable processing device available today or created in the future. For example, the client 140 may comprise a computer that includes an input device, such as a keypad, touch screen, or other device that can accept user information, and an output device that conveys information associated with the operation of the computing system 100.

In some implementations, functionality described as being performed by the computing system 100 may be performed by the client 140. For example, the computing system 100 may provide a client 140 with direct access to the projections calculated by the projection and adjustment module 120. As a result, some or all of the functionality described as being performed by the report module 122 may be performed by the client 140.

Figure 2:
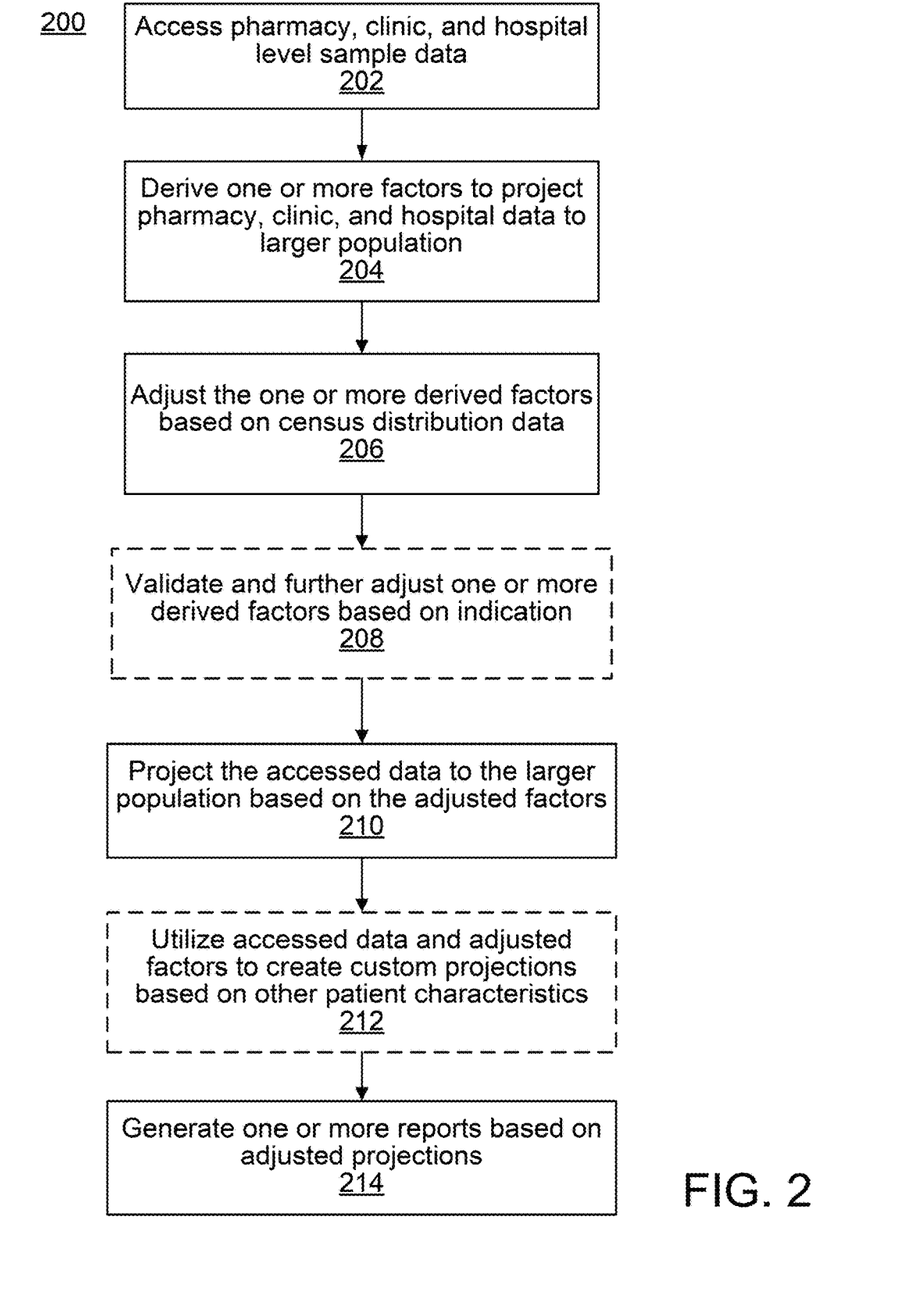
FIG. 2 is a flow chart for projecting patients having a medical condition by utilizing multiple sources of data.

FIG. 2 illustrates a flow chart 200 for projecting patients having a medical condition by utilizing multiple sources of data. For clarity of presentation, the description that follows generally describes method 200 in the context of FIG. 1. However, it will be understood that method 200 may be performed, for example, by any other suitable system, environment, software, and hardware, or a combination of systems, environments, software, and hardware as appropriate. For example, one or more of the data integration module 118, the projection and adjustment module 120, the report module 122, the client 140, or other computing device (not illustrated) can be used to execute method 200 and obtain any data from the memory of the client 140, the computing system 100, or the other computing device (not illustrated).

At 202, the projection and adjustment module 120 accesses sample data from one or more of at least three data channels: pharmacy data 110, clinic data 111, hospital data 112. As described previously, the pharmacy data 110, clinic data 111, and hospital data 112 may each represent a sample of data from across a geographic region. The data collected or received from the pharmacies, clinics, and hospitals included in each sample represents all or nearly all of the patient-based transactions conducted at each of these facilities. In other words, the pharmacy data 110 represents all or nearly all of the prescriptions filled by the sample pharmacies for which data has been collected. The clinic data 111 represents all or nearly all of the diagnoses made at the sample clinics for which data has been collected. The hospital data 112 represents all or nearly all of the treatment records generated at the sample hospitals for which data has been collected. Alternatively, one or more of the pharmacy data 110, clinic data 111, and/or hospital data 112 may be census-level data such that it is received from all or nearly all of the respective entities in the geographic area.

The projection and adjustment module 120 may also access payer data 113. The payer data 113 may also be sample data that is received from a subset of all health insurance companies in a geographic area. Alternatively, the payer data 113 may be census data that is received from all or nearly all of the health insurance companies serving a geographic area.

At 204, the projection and adjustment module 120 derives one or more factors used to project one or more of the pharmacy data 110, clinic data 111, and/or hospital data 112 from the sample of entities from which the data is collected to all of the entities (e.g., pharmacies, clinics, and/or hospitals) in a geographic area. In other words, the projection and adjustment module 120 utilizes comprehensive sample data from a subset of all data providers (e.g., pharmacies, clinics, and/or hospitals) in a geographic region and derives one or more factors or other statistical variables that relate the sample data to independent estimates of national patient data.

The projection and adjustment module 120 derives one or more factors for each of the channels of data (e.g., pharmacies, clinics, hospitals, and/or payers). Thus, the projection and adjustment module 120 facilitates multiple initial projections based on the derived factors. Because of the nature of the sample data and the independent estimates of national patient data, these projections may include sample biases. Accordingly, the projection and adjustment module 120 adjusts these one or more factors.

At 206, the projection and adjustment module 120 adjusts the one or more derived factors based on the distributor data 114. As previously described, the distributor data 114 may represent a census view of the pharmaceutical products purchased by all or nearly all of the pharmacies, clinics, and hospitals in a geographic region. Thus, the distributor data 114 may represent all of the pharmaceutical products going into the channels for which projections are being determined. Conversely, initial projections of the pharmacy data 110, clinic data 111, and hospital data 112 calculated based on the one or more factors derived in operation 204 include estimates of all the pharmaceutical products going out of the channels for which projections are being determined.

Specifically, the projected pharmacy data includes information about the pharmaceutical products being dispensed that the pharmacies in the geographic area, the projected clinic data includes information about the pharmaceutical products administered at clinics in the geographic area, and the projected hospital data includes information about the pharmaceutical products administered at hospitals in the geographic area. Accordingly, in some implementations, the projection and adjustment module 120 may be configured to compare the distributor data 114 with each of the projected pharmacy, clinic, and hospital data and adjust the one or more factors derived for each of these channels based on the comparison. For example, in some implementations, the projection and adjustment module 120 may adjust the factors derived for a given channel such that the amount of one or more pharmaceutical products being purchased by that channel (as reflected in the distributor data 114) corresponds to the estimated amount of the one or more pharmaceutical products being administered and/or distributed by that channel (as reflected in the projected data).

The projection and adjustment module 120 may make adjustments to the derived factors based on the channel data as a whole and/or may make adjustments to the derived factors for subsets of the channel data. For example, the projection and adjustment module 120 may divide the pharmacy data 110 based on the type of pharmacy providing the data, and may derive and/or adjust the factors based on this division. The projection and adjustment module 120 may divide the clinic data 111 based on the specialty group of the clinic providing the data, and may derive and/or adjust the factors based on this division. The projection and adjustment module 120 may divide the hospital data 112 into quintiles based on the number of patients served at the hospital providing the data, and may derive and/or adjust the factors based on this division.

Additionally or alternatively, the projection and adjustment module 120 may adjust the factors derived in operation 204 with distributor data 114 at both the national and sub-national level. For example, the projection and adjustment module 120 may initially adjust the factors for each channel at a nation level based on distributor data 114 for the nation. The projection and adjustment module 120 may then adjust the factors for each channel at a sub-nation level (e.g., state, county, zip code, or facility) based on distributor data 114 for that sub-national level. However, the order and number of adjustments made based on distributor data 114 may be altered, increased, or decreased, and is only limited by the level of detail available for the distributor data 114.

In some implementations, where the payer data 113 is sample data for a geographic area, as opposed to census data, the projection and adjustment module 120 may derive and adjust factors for projecting the payer data to all or nearly all of the payers serving a geographic area. To derive and adjust the one or more factors for the sample payer data, the projection and adjustment module 120 may use a process similar to the one described about for the pharmacy, clinic, and hospital data.

At 208, the projection and adjustment module 120 may optionally validate and/or further adjust the derived factors based on patient indications. An indication is a reason to use a certain test, medication, procedure, or surgery. In some implementations, the projection and adjustment module 120 may aggregate projected patients by drug and indication across the pharmacy data 110, clinic data 111, and hospital data 112. The projection and adjustment module 120 may then determine or receive information about differences between different sources of data (e.g. pharmacy data 110, clinic data 111, hospital data 112, and payer data 113), and adjust the one or more factors to provide a reliable indication distribution and trend. For example, in some implementation, the projection and adjustment module 120 may use patient indication information included in the payer data 113 as a target of comparison of patient indication information included in the pharmacy data 110, clinic data 111, and hospital data 112, and may adjust the factors derived for the pharmacy data 110, clinic data 111, and hospital data 112 based on the comparison.

At 210, the projection and adjustment module 120 uses the derived and adjusted factors to project prescription projection 126, clinic projection 128, and hospital projection 130. As described above, the pharmacy data 110, clinic data 111, and hospital data 112 may include patient linking identifiers, and the projection and adjustment module 120 may use these identifiers to correlate the patient projections from each channel, providing a view of patients across multiple channels.

At 212, the projection and adjustment module 120 may optionally integrate additional patient information (e.g., condition-specific information or consumer information) to the existing projections and project this additional information to the total population of patients. In some implementations, for example, the projection and adjustment module 120 may determine metastatic or stage status for a sample of oncology patients. The projection and adjustment module 120 may derive statistical models using the one or more factors derived and adjusted in operations 204 to 208 to project this metastatic or stage status to the total population of oncology patients in a geographic area. Similarly, the projection and adjustment module 120 may model any customized studies based on the one or more adjusted factors and the received pharmacy data 110, clinic data 111, hospital data 112, payer data 113, and distribution data 114.

At 214, the report module 122 generates reports based on the projections of the accessed data. As described above, the reports prepared by the report module may include one or more of the projections calculated by the projection and adjustment module 120 as well as any other data contained in the received pharmacy data 110, clinic data 111, hospital data 112, payer data 113, and distribution data 114. Moreover, the reports generated by the report module 122 may be requested by a client 140 and tailored to the needs of a particular user.

Figure 3:
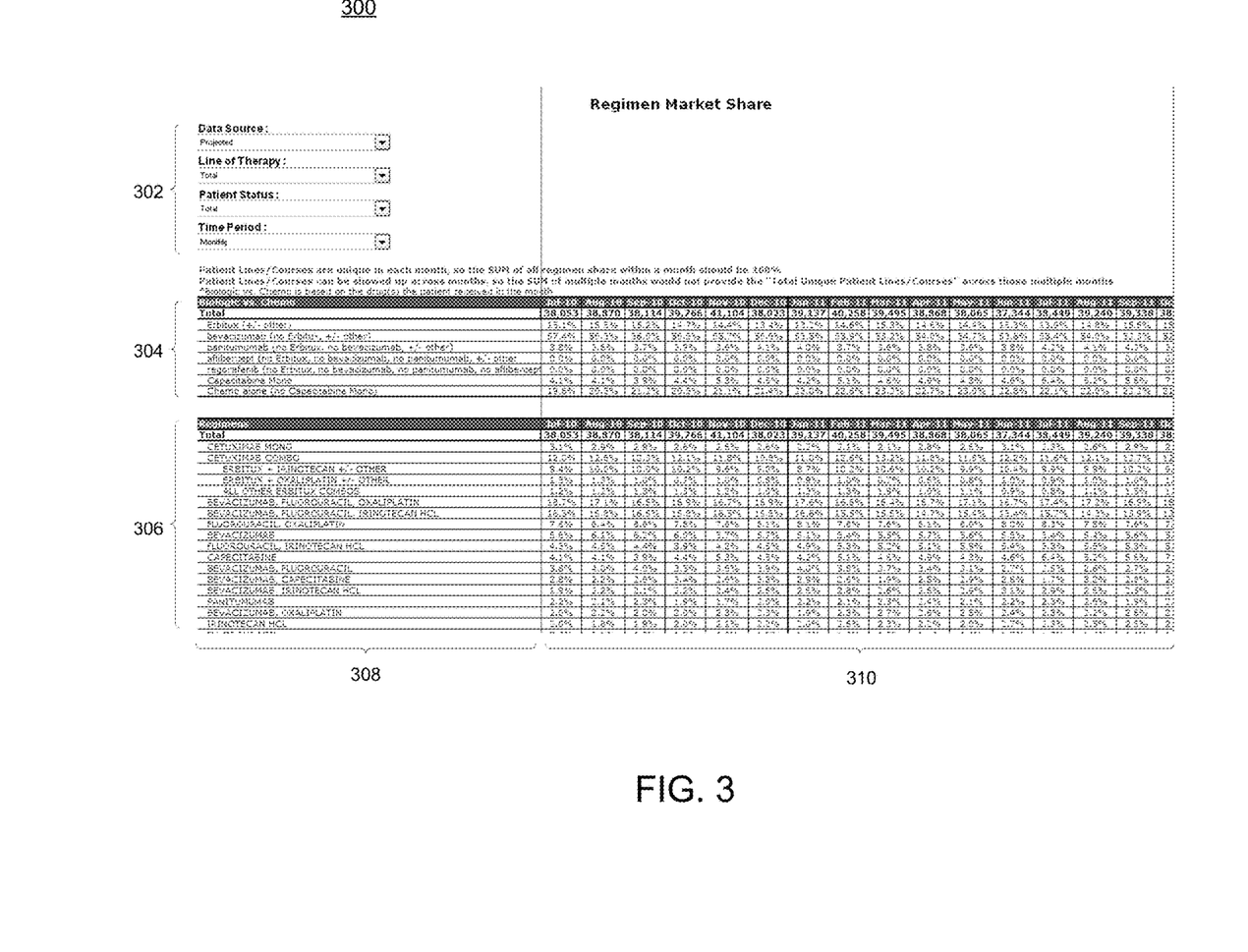
FIG. 3 illustrate example reports generated based on projection of patients.

FIG. 3 illustrates an example report 300 that may be generated by the report module 122 based on the projection of patients. The report illustrated in FIG. 3 is an example of a dynamic report, because the report illustrated in FIG. 3 includes controls that allow a user to alter and manipulate the report. FIG. 3 is not meant to limit the scope of the reports that may be generated by the report module 122. Rather, the report module 122 may generate reports that include similar information in a different format than that shown in FIG. 3 or may generate entirely different reports based on the information collected and generated by the system 100.

A user of a client 140 may log into the computer system 100 and request the report 300. For example, the user could open a web browser on the client, log into the computer system, and request the report 300. Alternatively, the report module 122 could communicate the report 300 through any appropriate means of communication with or without user request (e.g., the report could be produced on demand or scheduled). Moreover, though the report 300 is shown with a particular layout (i.e., a spreadsheet based format), the information included in report 300 could be presented in any format that would be useful to a user.

Report 300 is a nation report that presents the market share of various therapeutic regimens for oncology patients. Specifically, report 300 includes filtering controls 302. Filtering controls 302 allow a user to filter the information included in the report 300 by various criteria, including the source of data (e.g., a projection), a line of therapy, a patient status, and a period of time (e.g., a month). For example, if a user interacts with filtering control 302 to select the time period "monthly", the report 300 will display data in monthly increments. The processing necessary to filter the data and render the display of the report 300 based on the filtering controls 302 may be executed at either the client 140 or at the computer system 100 (by, for example, the report module 122). Additional filtering capability could also be added that permits a user to filter by any information stored by the computer system 100.

Rows 304 of the report show monthly projected numbers of patients treated by each pharmaceutical products of interest. Rows 306 of the report show monthly projected number of patients treated with different regimen. Column 308 of the report shows the drug description and regimen combination. Column 310 of the report shows the monthly projected number of patient share out of total cancel patients.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

What is claimed is:

1. A computer-implemented method, comprising:
    obtaining, from a first set of database systems over a distributed communication network and by a data integration module of a computer system, a stream of encrypted transaction data that includes one or more data fields for de-identified transaction profiles of multiple transaction sources that are located within a geographic region, wherein the computer system comprises the data integration module and a prediction module that communicates with the data integration module to determine at least one data projection;
    processing, by the data integration module, contents of the stream of encrypted transaction data to generate a structured aggregate data record, the processing comprising:
        determining, for each de-identified transaction profile from among the de-identified transaction profiles of the multiple transaction sources, a respective mapping that identifies data fields that correspond to the same transaction profile;
        generating, for each de-identified transaction profile and based on analysis of the stream of encrypted transaction data, a linking identifier for identifying transaction profile data corresponding to the same transaction profile and for removing at least a subset of duplicate transaction profile data included among the same transaction profiles;
        determining, for each de-identified transaction profile, a transaction source identifier based on the contents of the corresponding data fields that are identified by the respective mapping;
        generating, for each de-identified transaction profile and using the respective transaction source identifiers determined for each de-identified transaction profile, a respective database record that includes the corresponding data fields that are identified by the respective mapping and the linking identifier; and
        generating the structured aggregate data record, the structured aggregate data record including (i) transaction source identifiers determined for each of the de-identified transaction profiles, and (ii) the respective database records generated for each transaction source identifier, and wherein generating the structured aggregate data record includes removing, based on the linking identifier, a subset of data that is duplicated among the respective database records;
    determining, by the prediction module and based on the contents of the structured aggregate data record generated using the data integration module, one or more regression factors used to identify future transactions of the transaction sources within the geographic region;
    determining, by the prediction module and using the one or more regression factors, a first data projection that identifies one or more data fields for a set of future transactions of each of the transaction sources located within the geographic region;
    obtaining, from a second set of database systems over the distributed communication network and by the prediction module, a stream of distributor transaction data that includes one or more reference data fields associated with each of the transaction sources;
    comparing, by the prediction module, the one or more data fields for the set of future transactions identified by the first data projection to the one or more reference fields in the stream of distributor transaction data that are associated with each of the transaction sources;
    in response to comparing, identifying a sample bias in the first data projection based on information describing the set of future transactions identified by the first data projection that was determined using the one or mote regression factors, wherein the sample bias limits accuracy or reliability of the first data projection;
    determining an adjustment factor that: i) accounts for the sample bias in the first data projection based on information in the stream or distributor transaction data, and ii) improves accuracy or reliability in projections when used to determine a subsequent data projection;
    adjusting, by the prediction module, the one or more regression factors based on the adjustment factor that accounts for the sample bias in the first data projection;
    determining, by the prediction module and using the one or more adjusted regression factors, a second data projection that identifies one or more additional data fields for the set of future transactions of each of the transaction sources located within the geographic region, wherein the one or more additional data fields are not identified within the first data projection, and wherein the adjustment factor that accounts for the sample bias in the first data projection causes the second data projection to have improved accuracy or reliability relative to the first data projection; and
    generating, by a reporting module of the computer system that communicates with the prediction module, a report that includes at least the first and second data projections determined by the prediction module, the report being provided for output to a client device.

2. The method of claim 1, wherein:
    determining the one or more regression factors comprises determining different factors for each database system included within the first set of database systems;
    determining the first data projection comprises determining, for each database system included within the first set of database systems, a different projection based on the different regression factors for each database system included within the first set of database systems;
    comparing the one or more data fields identified by the first data projection to the one or more reference fields associated with each of the transaction sources comprises comparing the different projections determined for the database systems included within the first set of database systems; and
    adjusting the one or more regression factors comprises adjusting the one or more regression factors determined for each database system included within the first set of database systems based on the comparison of the different projections determined for the database systems included within the first set of database systems.

3. The method of claim 1, further comprising:
receiving claims data from one or more database systems associated with health insurance companies;
comparing one or more components of the second data projection to one or more components of the claims data received from database systems associated with health insurance companies; and
validating the second data projection based on the comparison of the one or more components of the second projection to the one or more components of the claims data received from database systems associated with health insurance companies.

4. The method of claim 1, wherein:
the de-identified transaction profiles each correspond to a patient located within the geographic region; and
the one or more data fields for the de-identified transaction profiles comprise a data field specifying metastatic and oncological stage data for a patient.

5. The method of claim 1, wherein:
the geographic region comprises a national area including sub-national segments;
comparing the one or more data fields identified by the first data projection to the one or more reference data fields associated with each of the transaction sources comprises:
identifying, for each of the one or more database fields identified by the first data projection, a particular sub-national segment from among the sub-national segments included in the national area;
identifying, for each of the one or more reference data fields, a particular sub-national segment from among the sub-national segments included in the national area; and
comparing, for each of the sub-national segments included in the national area, database fields and reference data fields identified to a particular sub-national segment.

6. The method of claim 1, wherein the stream of distributor transaction data obtained from the second set of database systems comprises pharmaceutical distribution data for pharmaceutical products associated with the de-identified transaction profiles of the multiple transaction sources.

7. The method of claim 1, wherein the multiple transaction sources that are located within the geographic region comprises at least one of a pharmacy, a hospital, or a medical clinic.

8. The method of claim 1, wherein determining the adjustment factor comprises:
determining the adjustment factor based on a current census view in the distributor transaction data that provides more detailed transaction information relative to the contents of the structured aggregate data record that cause the sample bias in the first data projection, wherein the more detailed transaction information describes item transactions across a region that is more expansive than the geographic region.

9. The method of claim 8, wherein the adjustment factor accounts for the sample bias and improves accuracy or reliability in projections by:
using the current census view in the distributor transaction data to determine the adjusted regression factors and to refine resulting projections about future transactions that are included in the second data projection.

10. A non-transitory computer-readable storage device encoded with a computer program, the program comprising instructions that when executed by one or more computers cause the one or more computers to perform operations comprising:
obtaining, from a first set of database systems over a distributed communication network and by a data integration module of a computer system, a stream of encrypted transaction data that includes one or more data fields for de-identified transaction profiles of multiple transaction sources that are located within a geographic region, wherein the computer system comprises the data integration module and a prediction module that communicates with the data integration module to determine at least one data projection;
processing, by the data integration module, contents of the stream of encrypted transaction data to generate a structured aggregate data record, the processing comprising:
determining, for each de-identified transaction profile from among the de-identified transaction profiles of the multiple transaction sources, a respective mapping that identifies data fields that correspond to the same transaction profile;
generating, for each de-identified transaction profile and based on analysis of the stream of encrypted transaction data, a linking identifier for identifying transaction profile data corresponding to the same transaction profile and for removing at least a subset of duplicate transaction profile data included among the same transaction profiles;
determining, for each de-identified transaction profile, a transaction source identifier based on the contents of the corresponding data fields that are identified by the respective mapping;
generating, for each de-identified transaction profile and using the respective transaction source identifiers determined for each de-identified transaction profile, a respective database record that includes the corresponding data fields that are identified by the respective mapping and the linking identifier; and
generating the structured aggregate data record, the structured aggregate data record including (i) transaction source identifiers determined for each of the de-identified transaction profiles, and (ii) the respective database records generated for each transaction source identifier, and wherein generating the structured aggregate data record includes removing, based on the linking identifier, a subset of data that is duplicated among the respective database records;
determining, by the prediction module and based on the contents of the structured aggregate data record generated using the data integration module, one or more regression factors used to identify future transactions of the transaction sources within the geographic region;
determining, by the prediction module and using the one or more regression factors, a first data projection that identifies one or more data fields for a set of future transactions of each of the transaction sources located within the geographic region;
obtaining, from a second set of database systems over the distributed communication network and by the prediction module, a stream of distributor transaction data that includes one or more reference data fields associated with each of the transaction sources;
comparing, by the prediction module, the one or more data fields for the set of future transactions identified by the first data projection to the one or more reference fields in the stream of distributor transaction data that are associated with each of the transaction sources;

in response to comparing, identifying a sample bias in the first data projection based on information describing the set of future transactions identified by the first data projection that was determined using the one or mote regression factors, wherein the sample bias limits accuracy or reliability of the first data projection, determining an adjustment factor that: i) accounts for the sample bias in the first data projection based on information in the stream or distributor transaction data, and ii) improves accuracy or reliability in projections when used to determine a subsequent data projection;

adjusting, by the prediction module, the one or more regression factors based on the adjustment factor that accounts for the sample bias in the first data projection;

determining, by the prediction module and using the one or more adjusted regression factors, a second data projection that identifies one or more additional data fields for the set of future transactions of each of the transaction sources located within the geographic region, wherein the one or more additional data fields are not identified within the first data projection, and wherein the adjustment factor that accounts for the sample bias in the first data projection causes the second data projection to have improved accuracy or reliability relative to the first data projection; and generating, by a reporting module of the computer system that communicates with the prediction module, a report that includes at least the first and second data projections determined by the prediction module, the report being provided for output to a client device.

11. The device of claim 10, wherein:

determining the one or more regression factors comprises determining different factors for each database system included within the first set of database systems;

determining the first data projection comprises determining, for each database system included within the first set of database systems, a different projection based on the different regression factors for each database system included within the first set of database systems;

comparing the one or more data fields identified by the first data projection to the one or more reference fields associated with each of the transaction sources comprises comparing the different projections determined for the database systems included within the first set of database systems; and adjusting the one or more regression factors comprises adjusting the one or more regression factors determined for each database system included within the first set of database systems based on the comparison of the different projections determined for the database systems included within the first set of database systems.

12. The device of claim 10, wherein the operations further comprise:

receiving claims data from one or more database systems associated with health insurance companies;

comparing one or more components of the second data projection to one or more components of the claims data received from database systems associated with health insurance companies; and validating the second data projection based on the comparison of the one or more components of the second projection to the one or more components of the claims data received from database systems associated with health insurance companies.

13. The device of claim 10, wherein:

the de-identified transaction profiles each correspond to a patient located within the geographic region; and the one or more data fields for the de-identified transaction profiles comprise a data field specifying metastatic and oncological stage data for a patient.

14. The device of claim 10, wherein:

the geographic region comprises a national area including sub-national segments;

comparing the one or more data fields identified by the first data projection to the one or more reference data fields associated with each of the transaction sources comprises:

identifying, for each of the one or more database fields identified by the first data projection, a particular sub-national segment from among the sub-national segments included in the national area;

identifying, for each of the one or more reference data fields, a particular sub-national segment from among the sub-national segments included in the national area; and comparing, for each of the sub-national segments included in the national area, database fields and reference data fields identified to a particular sub-national segment.

15. The device of claim 10, wherein the multiple transaction sources that are located within the geographic region comprises at least one of a pharmacy, a hospital, or a medical clinic.

16. A system comprising:

one or more processors; and one or more storage mediums storing instructions that, when executed by the one or more processors, cause the one or more processors to perform operations comprising:

obtaining, from a first set of database systems over a distributed communication network and by a data integration module of a computer system, a stream of encrypted transaction data that includes one or more data fields for de-identified transaction profiles of multiple transaction sources that are located within a geographic region, wherein the computer system comprises the data integration module and a prediction module that communicates with the data integration module to determine at least one data projection;

processing, by the data integration module, contents of the stream of encrypted transaction data to generate a structured aggregate data record, the processing comprising:

determining, for each de-identified transaction profile from among the de-identified transaction profiles of the multiple transaction sources, a respective mapping that identifies data fields that correspond to the same transaction profile;

generating, for each de-identified transaction profile and based on analysis of the stream of encrypted transaction data, a linking identifier for identifying transaction profile data corresponding to the same transaction profile and for removing at least a subset of duplicate transaction profile data included among the same transaction profiles;

determining, for each de-identified transaction profile, a transaction source identifier based on the contents of the corresponding data fields that are identified by the respective mapping;

generating, for each de-identified transaction profile and using the respective transaction source identifiers determined for each de-identified transaction profile, a respective database record that includes the corresponding data fields that are identified by the respective mapping and the linking identifier; and generating the structured aggregate data record, the structured aggregate data record including (i) transaction source identifiers determined for each of the de-identified transaction profiles, and (ii) the respective database records generated for each transaction source identifier, and wherein generating the structured aggregate data record includes removing, based on the linking identifier, a subset of data that is duplicated among the respective database records;

determining, by the prediction module and based on the contents of the structured aggregate data record generated using the data integration module, one or more regression factors used to identify future transactions of the transaction sources within the geographic region;

determining, by the prediction module and using the one or more regression factors, a first data projection that identifies one or more data fields for a set of future transactions of each of the transaction sources located within the geographic region;

obtaining, from a second set of database systems over the distributed communication network and by the prediction module, a stream of distributor transaction data that includes one or more reference data fields associated with each of the transaction sources;

comparing, by the prediction module, the one or more data fields for the set of future transactions identified by the first data projection to the one or more reference fields in the stream of distributor transaction data that are associated with each of the transaction sources;

in response to comparing, identifying a sample bias in the first data projection based on information describing the set of future transactions identified by the first data projection that was determined using the one or mote regression factors, wherein the sample bias limits accuracy or reliability of the first data projection, determining an adjustment factor that: i) accounts for the sample bias in the first data projection based on information in the stream or distributor transaction data, and ii) improves accuracy or reliability in projections when used to determine a subsequent data projection;

adjusting, by the prediction module, the one or more regression factors based on the adjustment factor that accounts for the sample bias in the first data projection;

determining, by the prediction module and using the one or more adjusted regression factors, a second data projection that identifies one or more additional data fields for the set of future transactions of each of the transaction sources located within the geographic region, wherein the one or more additional data fields are not identified within the first data projection, and wherein the adjustment factor that accounts for the sample bias in the first data projection causes the second data projection to have improved accuracy or reliability relative to the first data projection; and generating, by a reporting module of the computer system that communicates with the prediction module, a report that includes at least the first and second data projections determined by the prediction module, the report being provided for output to a client device.

17. The system of claim 16, wherein:

determining the one or more regression factors comprises determining different factors for each database system included within the first set of database systems;

determining the first data projection comprises determining, for each database system included within the first set of database systems, a different projection based on the different regression factors for each database system included within the first set of database systems;

comparing the one or more data fields identified by the first data projection to the one or more reference fields associated with each of the transaction sources comprises comparing the different projections determined for the database systems included within the first set of database systems; and adjusting the one or more regression factors comprises adjusting the one or more regression factors determined for each database system included within the first set of database systems based on the comparison of the different projections determined for the database systems included within the first set of database systems.

18. The system of claim 16, wherein the operations further comprise:

receiving claims data from one or more database systems associated with health insurance companies;

comparing one or more components of the second data projection to one or more components of the claims data received from database systems associated with health insurance companies; and validating the second data projection based on the comparison of the one or more components of the second projection to the one or more components of the claims data received from database systems associated with health insurance companies.

19. The system of claim 16, wherein:

the de-identified transaction profiles each correspond to a patient located within the geographic region; and the one or more data fields for the de-identified transaction profiles comprise a data field specifying metastatic and oncological stage data for a patient.

20. The system of claim 16, wherein:

the geographic region comprises a national area including sub-national segments;

comparing the one or more data fields identified by the first data projection to the one or more reference data fields associated with each of the transaction sources comprises:

identifying, for each of the one or more database fields identified by the first data projection, a particular sub-national segment from among the sub-national segments included in the national area;

identifying, for each of the one or more reference data fields, a particular sub-national segment from among the sub-national segments included in the national area; and comparing, for each of the sub-national segments included in the national area, database fields and reference data fields identified to a particular sub-national segment.

* * * * *

UNITED STATES PATENT AND TRADEMARK OFFICE
CERTIFICATE OF CORRECTION

PATENT NO. : 10,185,809 B1
APPLICATION NO. : 14/054272
DATED : January 22, 2019
INVENTOR(S) : Li Zhou, Xiaoping Cai and Timothy A. Hughes It is certified that error appears in the above-identified patent and that said Letters Patent is hereby corrected as shown below:

In the Claims

Column 16, Line 22, In Claim 1, delete "mote" and insert -- more --.

Column 19, Line 6, In Claim 10, delete "mote" and insert -- more --.

Column 21, Line 38, In Claim 17, delete "mote" and insert -- more --.

Column 21, Line 40, In Claim 17, delete "projection," and insert -- projection; --.

Signed and Sealed this
Nineteenth Day of March, 2019

Andrei Iancu
*Director of the United States Patent and Trademark Office*